(12) United States Patent
Gold et al.

(10) Patent No.: US 10,081,527 B2
(45) Date of Patent: Sep. 25, 2018

(54) COVER REMOVAL SYSTEM FOR USE IN CONTROLLED ENVIRONMENT ENCLOSURES

(71) Applicant: Vanrx Pharmasystems Inc., Burnaby (CA)

(72) Inventors: Ross M. Gold, North Vancouver (CA); Steve Sang Joon, Oakville (CA); Christopher A. Procyshyn, Surrey (CA); Jeroen Immerzeel, Squamish (CA); Paul Nowaczyk, Welland (CA)

(73) Assignee: VANRX PHARMASYSTEMS INC., Burnaby (CA)

( * ) Notice: Subject to any disclaimer, the term of this patent is extended or adjusted under 35 U.S.C. 154(b) by 356 days.

(21) Appl. No.: 14/398,538

(22) PCT Filed: May 3, 2013

(86) PCT No.: PCT/US2013/039455
§ 371 (c)(1),
(2) Date: Nov. 3, 2014

(87) PCT Pub. No.: WO2103/166379
PCT Pub. Date: Nov. 7, 2013

(65) Prior Publication Data
US 2016/0251206 A1    Sep. 1, 2016

Related U.S. Application Data

(60) Provisional application No. 61/642,430, filed on May 3, 2012.

(51) Int. Cl.
*B67B 7/14* (2006.01)
*B65B 57/02* (2006.01)
(Continued)

(52) U.S. Cl.
CPC .............. *B67B 7/14* (2013.01); *B65B 57/02* (2013.01); *B65B 69/00* (2013.01); *B67B 7/38* (2013.01)

(58) Field of Classification Search
CPC ......... B65B 43/40; B65B 43/26; B65B 43/30; B65B 69/00; B65B 69/003; B25J 21/00;
(Continued)

(56) References Cited

U.S. PATENT DOCUMENTS 1,331,207 A * 2/1920 Mouneyrat .............. B25J 21/02
422/199
2,694,324 A * 11/1954 Goldsmith ................ B67B 7/14
81/3.27
(Continued)

FOREIGN PATENT DOCUMENTS

DE    4419475        7/1995
DE    4419475 A1 * 12/1995  ............. B65B 69/00
WO    2011036190      3/2011

OTHER PUBLICATIONS

Machine translation of DE4419475A1 included as reference.*
(Continued)

*Primary Examiner* — Hemant M Desai
*Assistant Examiner* — Lucas Palmer
(74) *Attorney, Agent, or Firm* — Kevin R. Erdman; Brannon Sowers & Cracraft PC

(57) ABSTRACT

An apparatus and method are presented for removing container covers within a controlled environment enclosure without using gloves. The apparatus comprises an articulated arm apparatus and a gripping apparatus and can further comprise a controller. The articulated arm apparatus can be configurable for holding and moving a container in three dimensions; and the gripping apparatus can be configured for gripping a container cover sealing the container. The method comprises moving the container using the articu-
(Continued)

lated arm apparatus while holding a gripping area of the container cover substantially stationary using the gripping apparatus. The apparatus can further comprise a sensor configured for supplying information to the controller for determining the location of the container cover gripping area and an orientation of the container cover. The method can further comprise inspecting the container cover using the sensor. The container can be moved along a path and within a space determined by the controller.

21 Claims, 9 Drawing Sheets

(51) Int. Cl.
    *B65B 69/00*      (2006.01)
    *B67B 7/00*      (2006.01)

(58) Field of Classification Search
    CPC .... B67B 7/00; B67B 7/14; B67B 7/38; B67B 2201/08
    USPC ........ 414/729–741, 800, 816; 53/492, 381.1, 53/381.2, 381.4
    See application file for complete search history.

(56) References Cited

U.S. PATENT DOCUMENTS

| | | | | |
|---|---|---|---|---|
| 2,735,602 A * | 2/1956 | Wise | ............ | B08B 9/0848 53/381.4 |
| 2,995,883 A * | 8/1961 | Aubry | ............ | B65B 43/40 53/109 |
| 5,048,259 A * | 9/1991 | Cox | ............ | B65B 7/2842 53/132.1 |
| 5,370,019 A * | 12/1994 | Sartell | ............ | B67B 7/182 81/3.2 |
| 5,657,617 A * | 8/1997 | Allen | ............ | B65B 7/2842 53/284 |
| 5,934,859 A | 8/1999 | Goetzelmann | | |
| 6,503,130 B2 * | 1/2003 | Lim | ............ | B24B 37/34 156/716 |
| 6,983,721 B2 * | 1/2006 | Gabriel | ............ | A01K 1/031 119/456 |
| 7,565,786 B2 * | 7/2009 | Miksch | ............ | B65B 69/00 53/381.4 |
| 7,783,383 B2 * | 8/2010 | Eliuk | ............ | A61J 1/20 141/1 |
| 8,349,129 B2 * | 1/2013 | Blanchard | ............ | B32B 43/006 156/707 |
| 8,408,860 B2 * | 4/2013 | Gupta | ............ | C12M 23/10 414/411 |
| 2003/0009985 A1 * | 1/2003 | Close | ............ | B65B 7/28 53/76 |
| 2003/0120387 A1 * | 6/2003 | Sherwin | ............ | B25J 15/0052 700/245 |
| 2005/0115982 A1 * | 6/2005 | Gregson, Jr. | ............ | B65B 69/00 222/1 |
| 2005/0160704 A1 * | 7/2005 | Miksch | ............ | B65B 69/00 53/492 |
| 2005/0205204 A1 * | 9/2005 | Kurosawa | ............ | H01L 21/67132 156/716 |
| 2006/0136095 A1 * | 6/2006 | Rob | ............ | A61J 1/20 700/245 |
| 2006/0219359 A1 * | 10/2006 | Miyamoto | ............ | B29C 63/0013 156/716 |
| 2008/0017311 A1 * | 1/2008 | Yoshioka | ............ | H01L 21/67132 156/716 |
| 2008/0185100 A1 * | 8/2008 | Jang | ............ | B32B 43/006 156/714 |
| 2008/0236743 A1 * | 10/2008 | Kye | ............ | B29C 63/0013 156/714 |
| 2008/0245483 A1 * | 10/2008 | Toyoshima | ............ | B32B 43/006 156/763 |
| 2009/0208316 A1 * | 8/2009 | Mayer | ............ | B65B 69/00 414/729 |
| 2009/0287354 A1 * | 11/2009 | Choi | ............ | B25J 9/1633 700/261 |
| 2010/0107570 A1 * | 5/2010 | Khan | ............ | B65B 9/18 53/479 |
| 2014/0157722 A1 * | 6/2014 | Iwamoto | ............ | H01L 21/67772 53/111 R |
| 2016/0023793 A1 * | 1/2016 | Wilson | ............ | B65B 69/00 53/381.4 |
| 2016/0200461 A1 * | 7/2016 | Broadbent | ............ | B65B 55/04 53/426 |

OTHER PUBLICATIONS

Communication about intention to grant a European patent, including Text Intended for Grant; EP137851473; Feb. 20, 2017.
Supplementary European search report, and European search opinion; EP137851473; dated Dec. 23, 2015.
International preliminary report on patentability; PCT/US2013/039455; dated Aug. 22, 2013.
International search report; PCT/US2013/039455; dated Aug. 22, 2013.

* cited by examiner

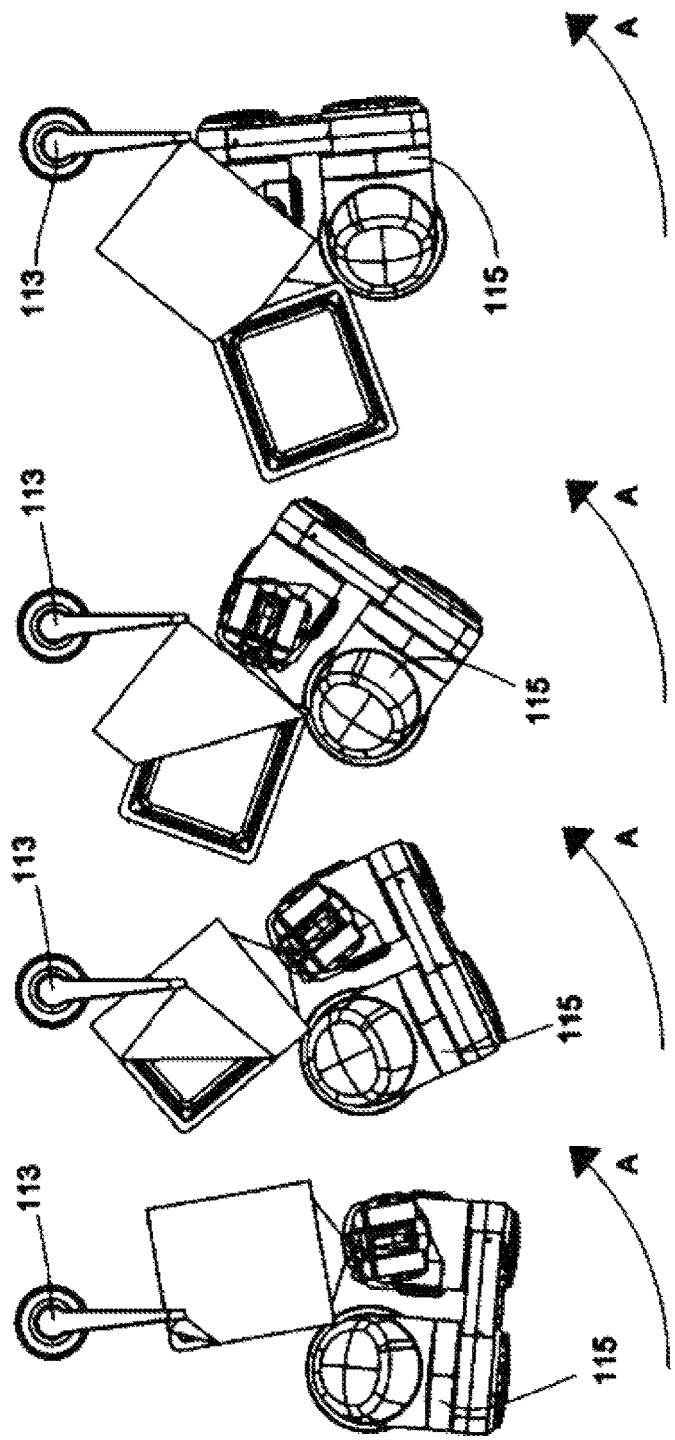

COVER REMOVAL SYSTEM FOR USE IN CONTROLLED ENVIRONMENT ENCLOSURES

FIELD OF THE INVENTION

This document relates generally to controlled environment enclosures and in particular to a method and apparatus for removing covers from sealed containers in controlled environment enclosures.

BACKGROUND OF THE INVENTION

Controlled environment enclosures are known in the art and are used, for example, for containment of hazardous materials or to provide controlled environments with limited numbers of particulates.

In the art, controlled environment enclosures are typically fitted with ports for transfer of materials in and out of the enclosure and the ports are fitted with gloves for manual manipulation of equipment, parts or materials inside the enclosure. Such gloves are subject to significant risk of puncture, the consequences of which can be severe.

In some examples known in the art the controlled environment enclosure is also used to limit exposure to viable particulates such a bacteria and fungi. The controlled environment enclosures may be required for aseptic processing of cell cultures or for the manufacture of pharmaceutical products, medical devices, food or food ingredients. In such applications the requirement is for the controlled environment enclosure to be decontaminated. This can be done thermally using steam or chemically using chemical agents. Suitable chemical agents known in the art include hydrogen peroxide, ozone, beta-propiolactone, aziridine, formaldehyde, chlorine dioxide, ethylene oxide, propylene oxide, and peracetic acid. In most cases the decontamination and sterilization operations have to be preceded by a cleaning process. Such cleaning processes have the function of removing major contamination by simple mechanical and chemical action.

In some prior art examples the controlled environment also contains automated equipment. Such automated equipment can include machines for manipulation of parts or as containers, including test tubes, roller bottles, cell culture dishes, bottles, vials, ampoules and syringes. Typical examples of such manipulations are inspection, filling and capping.

Parts to be manipulated in controlled environment enclosures can be packaged in a container such as a tub. The container can be closed with a cover consisting of a sheet of flexible material, which generally is heat sealed to the container. The container and contents are decontaminated using a chemical agent, plasma or radiation.

The automated equipment located in the controlled environment is typically of such a size and complexity that it cannot be operated fully automatically without human intervention. Such human intervention typically requires the use of gloves with the associated risk of puncture. A typical example of human intervention that involves the use of gloves is the removal of container covers.

SUMMARY OF THE INVENTION

In view of the above background there remains a need for an apparatus and method for removal of container covers within controlled environments that does not require human intervention via the use of gloves.

In a first aspect a method is presented for removing within a controlled environment enclosure a container cover from a sealed container, the sealed container sealed by the container cover, the method comprising moving the container while holding a gripping area of the container cover substantially stationary. The moving of the container comprises holding the container with an articulated arm apparatus disposed within the controlled environment whilst removing the container cover by a first manipulation of the articulated arm apparatus. The method further comprises a second manipulating of the articulated arm apparatus to position along a trajectory the sealed container within a reach of a gripping apparatus disposed within the controlled environment, and gripping the gripping area with the gripping apparatus.

The positioning of the sealed container comprises placing the gripping area of the container cover between two gripping elements of the gripping apparatus, the first and second of the two gripping elements respectively comprising first and second mutually parallel and mutually engagable grip surfaces. The method further comprises rotating at least one of the gripping elements. The positioning of the gripping area can comprise placing the gripping area proximate and substantially facing the first grip surface. The rotating of at least one of the gripping elements can comprise moving the second of the two gripping elements in a plane substantially parallel to the first grip surface.

The positioning of the container can further comprise straightening the gripping area if the gripping area is bent toward the first grip surface by contacting to the first grip surface to one of the gripping area and a part of the cover in contact with the gripping area. The moving of the second gripping element can comprise straightening the gripping area if the gripping area is bent toward the second gripping element by contacting the second grip surface to the other of the gripping area and the part of the cover in contact with the gripping area.

The method can further comprise lowering the container or rotating the container about an axis substantially in the plane of the cover. This is done by a third manipulating of the articulated arm apparatus. The rotating or raising of the gripping area is to an extent that allows the gripping apparatus to remain clear of the container during the removing the container cover.

The removing the container cover can be removing the container cover simultaneously along two edges of the container. The first manipulating of the articulated arm apparatus can comprise moving the container with respect to the gripping apparatus. Moving the container with respect to the gripping apparatus can comprise moving the container substantially diagonally with respect to the gripping apparatus. The moving the container with respect to the gripping apparatus can comprise moving the container along a predetermined path within a predetermined space. One or both of the predetermined path and the predetermined space can be determined using a controller. The predetermined path can be a circular path.

The trajectory of the container can be based on information obtained from a sensor. The information can comprise one or both of position information and orientation information about the gripping area.

The method can further comprise inspecting the container cover using a sensor. The method can further comprise selecting an alternative gripping area of the container cover based on the inspecting; gripping the alternative gripping area with the gripping apparatus; and removing the container cover by moving the container.

The method can further comprise moving the gripping apparatus away from an operational area of the articulated arm apparatus after removing the container cover.

In a further aspect there is provided an apparatus comprising a controlled environment enclosure; and within the controlled environment enclosure an articulated arm apparatus and a rotary gripping apparatus. The articulated arm apparatus can be configurable for holding and moving a container in three dimensions; and the rotary gripping apparatus can be configured for gripping a gripping area of a container cover sealing the container. The rotary gripping apparatus can comprise two gripping elements having facing mutually engagable surfaces, at least one of the two gripping elements being rotatable about a common axis with the other of the two gripping elements to grip the gripping area of the container cover between the two facing mutually engagable surfaces. The articulated arm apparatus can comprise at least two arm segments, at least one arm segment being configurable to hold the container.

The articulated arm apparatus and the rotary gripping apparatus can be separated by a distance large enough for the gripping apparatus to not interfere with the working of the articulated arm apparatus. The apparatus can further comprise a controller for controlling at least the articulated arm apparatus and the gripping apparatus. The moving the container can be moving the container along a path that is determined by the controller and the moving the container is contained within a space determined by the controller.

The apparatus can further comprise a sensor configured for supplying information to the controller for determining at least one of a location of the container cover gripping area and an orientation of the container cover. The articulated arm apparatus can be at least one of automatically controlled and reprogrammable. The gripping apparatus can be at least one of automatically controlled and reprogrammable.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 5 shows a top view perspective of an articulated arm apparatus and gripping apparatus near an initial stage of removal of a cover from a container.

FIG. 6 shows a top view perspective of an articulated arm apparatus and gripping apparatus at a first intermediate stage of removal of a container cover from a container.

FIG. 7 shows a top view perspective of an articulated arm apparatus and gripping apparatus at a second intermediate stage of removal of a container cover from a container.

FIG. 8 shows a top view perspective of an articulated arm apparatus and gripping apparatus at near complete stage of removal of a container cover from a container

DETAILED DESCRIPTION

Figure 1:
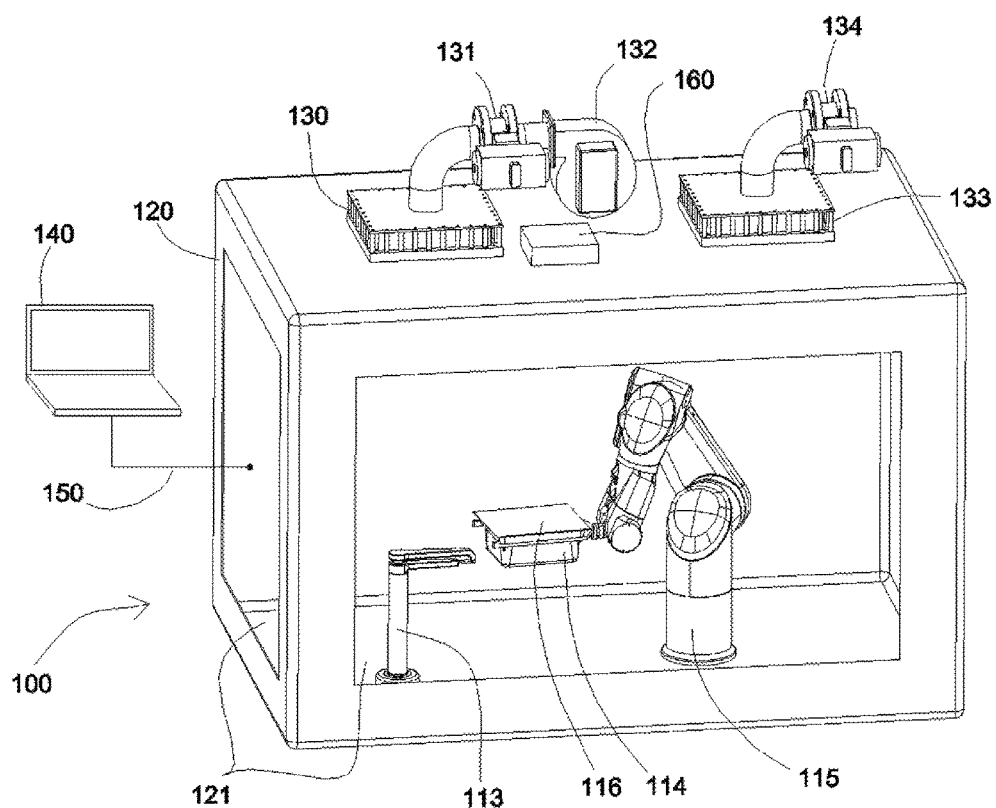
FIG. 1 shows a controlled environment enclosure containing an articulated arm apparatus for handling of containers and an apparatus for gripping of container covers.

FIG. 1 shows an apparatus 100 comprising a controlled environment enclosure 120, a gripping apparatus 113 and an articulated arm apparatus 115, both inside the controlled environment enclosure 120 and arranged for positioning and relocation of a container 114 within the controlled environment enclosure 120 without requiring direct human intervention and the associated use of gloves. Container 114 can be, for example, a tub. The term "tub" as used herein is used to describe any container suitable for holding parts, trays of nested arrangements of parts, a stack of trays with nested arrangements of parts, or combinations thereof.

The apparatus 100 can further comprise of a sensor 160 for sensing the container 114.

The controlled environment enclosure 120 can comprise windows 121, an inlet filter 130, an inlet valve 131, a blower 132, an outlet filter 133 and an outlet valve 134. The characteristics of blower 132, inlet filter 130, and outlet filter 133 are chosen to yield a controlled environment inside controlled environment enclosure 120. The contents of the controlled environment enclosure 120 can be protected by airflow while having one or more openings (not shown).

In another embodiment the controlled environment enclosure 120 can be fully sealed and be operated at a positive or negative pressure differential relative to the surroundings. Those skilled in the art will understand that several other filter and blower arrangements can be used to establish a controlled environment inside controlled environment enclosure 120. A suitable controlled environment can be obtained, for example without limitation, by means of any one or more of turbulent airflow, horizontal unidirectional airflow and vertical unidirectional airflow.

The operation of the gripping apparatus 113 and the articulated arm apparatus 115 is controlled by a means located outside of environment enclosure 120. In some embodiments the means of controlling apparatus 113, apparatus 115 and enclosure 120 require a local or remote operator input device such as joy stick control, push button control, emergency stop, touch screen human machine interface, keyboard, mouse, handheld device or the like. Typically one or more of such input devices are connected to a controller 140. In FIG. 1, a laptop computer programmed with suitable software is shown as an example of controller 140. In other embodiments controller 140 can be a variety of other means such as operator interface panel, programmable logic controller, programmable automation controller, a desktop computer or a remote I/O module with embedded logic functions. In some embodiments the controller 140 can consist of a plurality of the aformentioned controllers.

The controller 140 provides control instructions to apparatus 100 over control line 150. Control line 140 is a schematic representation of all of the required mechanical linkages, electrical wiring, pneumatic, hydraulic and wireless connections to operate apparatus 100.

The container 114 can be manipulated inside the controlled environment enclosure 120 by mechanical means, for example, an articulated arm apparatus 115. Suitable robotic arm manipulation systems for mechanically manipulating the container 114 include, but are not limited to, 6-axis robotic arms, Selective Compliant Articulated Robot Arm (SCARA) systems, r-theta robots, and assemblies of linear actuators and rotary actuators, or combinations thereof.

In one embodiment of the apparatus 100 the articulated arm apparatus 115 can be the articulated arm apparatus described in U.S. Provisional Patent Application 61/596,698, which is incorporated herein by reference.

The controlled environment enclosure 120, in some examples, includes a sensor 160 for sensing the container 114 and a container cover 116 for the container 114. In the example shown in FIG. 1 the sensor is mounted to the top surface of the controlled environment enclosure 120. In other embodiments it can be mounted at another suitable location to monitor the interior of controlled environment enclosure 120. The sensor 160, in one example is an optical sensor. In other examples the sensor 160 can be one of a variety of other types of sensors, such as a camera system, a laser system or an ultrasonic sensing system. In yet other examples the sensor 160 is an assembly that consists of a plurality of sensing elements. The sensor 160 has a sensing cone (not shown) or multiple sensing cones than can cover a small, a large area or both; depending on the characteristics of the sensor 160 used.

In other embodiments of this invention the controlled environment chamber 120 contains articulated arm apparatus 115 plus at least one further articulated arm apparatus (not shown in the interest of clarity). The additional at least one further articulated arm apparatus can be used, for example, for activities that can follow removal of the container cover 116 from the container 114. Apparatus 100 can be used for functions preceding the function of the filling system described in U.S. patent application Ser. No. 12/393,183, which is incorporated herein by reference.

In yet another embodiment gripping apparatus 113 is added to a filling system as described in U.S. Patent Application 61/033,682, with element 30 of U.S. Patent Application 61/033,682 as the equivalent of articulated arm apparatus 115 of the present specification, chamber 20 of U.S. Patent Application 61/033,682 as the equivalent of controlled environment enclosure 120 of the present specification, and optical sensor 12 of U.S. Patent Application 61/033,682 as the equivalent of sensor 160 of the present specification. U.S. Patent Application 61/033,682 is hereby incorporated by reference.

The articulation of arm apparatus 115 can be remoted operated by the operator. In another embodiment the articulated arm apparatus 115 can be an automatically controlled articulated arm. In yet another embodiment the articulated arm apparatus can be a reprogrammable automatically controlled articulated arm.

Figures 2, 3:
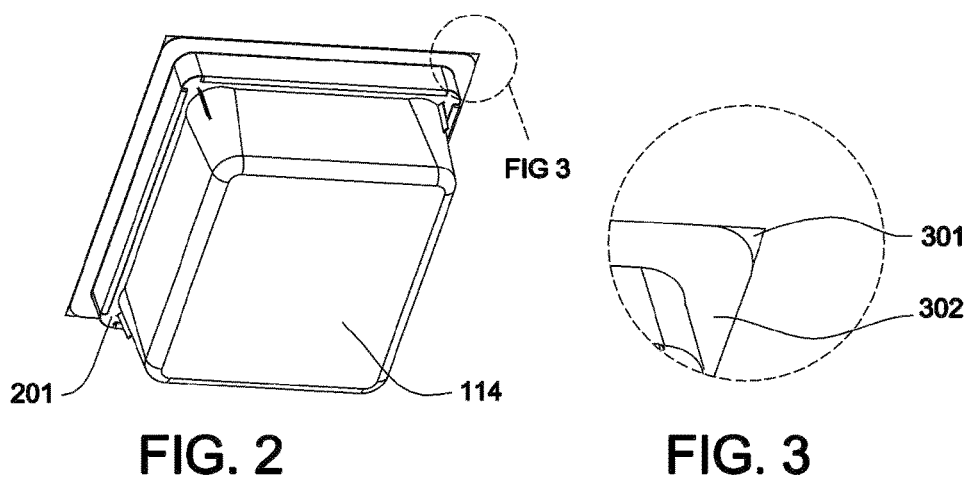
FIG. 2 shows an example of a container.
FIG. 3 shows a detail view of a container showing an example of the cover extending outside the outline of the top surface of the container.

FIG. 2 shows a bottom view of an example of the container 114. The container 114 can be made of a metal, glass, plastic or a composite material, but typically the tub 114 is a single use thin walled container. Thin walled single use containers are typically made by a low cost process, such as thermoforming or injection molding. As shown in FIG. 2, the container 114 can have features such as tapered sidewalls that assist in manufacturability, but are more difficult to hold than an object with rigid parallel walls. All four walls forming the sides of the container 114 can have a step 201.

FIG. 3 shows a detail view of container 114. The kind of container 114 typically employed in the pharmaceutical industry is characterized by a top lip 302 that provides a surface area for a sealed connection to the container cover 116. The term "cover" is used here to describe any surface material, including but not limited to a flexible sheet made of plastic material, a polymeric membrane or an impermeable laminated foil.

The container cover 116 can extend outside the outline of the top lip 302 of the tub 114 in at least one location, and typically extends outside the outline of the top lip 302 in a plurality of locations. The at least one area of container cover 116 that extends outside the outline of the top lip 302 provides a gripping area 301 that can be used as access for clamping. Clamping on the gripping area 301 can be complicated by the flexibility of the material of the container cover 116. The gripping area 301 can be level, bent upwards, or bent downwards.

Figure 4:
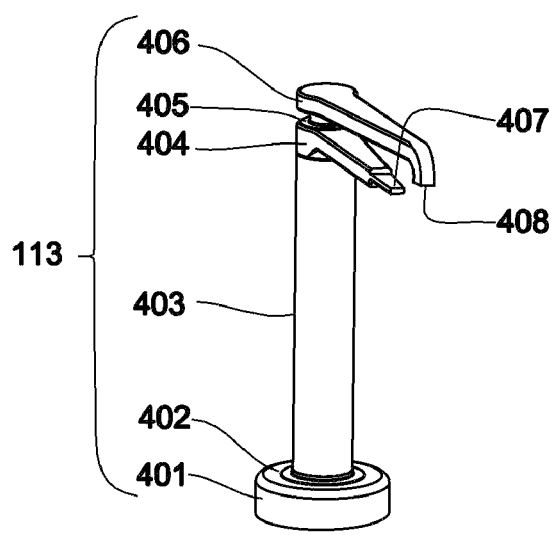
FIG. 4 shows a gripping apparatus with gripping jaws partially opened.

FIG. 4 shows an example embodiment of the gripping apparatus 113. An upper arm 406 is rotatably connected to a main shaft 403 by a radial seal 405. The main shaft 403 is rigidly connected to a lower arm 404 by a fully sealed joint. The main shaft 403 is rotatably connected to a base flange 401 by a radial seal 402. The base flange 401 is sealably connected to controlled environment enclosure 120. The tip of lower arm 404 and the tip of upper arm 406 have mutually facing and mutually engagable grip surfaces 407 and 408 respectively such that the mutually facing flat grip surfaces 407 and 408 are mutually engagable in the absence of any material, such as container cover material, being disposed between the surfaces. The grip surface 407 can be an upper surface of the tip of lower arm 404 and the grip surface 408 can be a lower surface of the tip of the upper arm 406.

In one embodiment of the gripping apparatus 113 the lower arm 404 is stationary and upper arm 406 is rotatable about a cylindrical axis of main shaft 403. In another embodiment of the gripping apparatus 113 the upper arm 406 is stationary and lower arm 404 is rotatable about the cylindrical axis of main shaft 403. In yet a further embodiment both upper arm 406 and lower arm 404 are rotatable about the cylindrical axis of main shaft 403.

The gripping apparatus 113 can be remotely operated by the operator. In another embodiment the gripping apparatus 113 can be automatically controlled. In yet another embodiment the gripping apparatus 113 can be a reprogrammable automatically controlled gripping apparatus.

We now describe at the hand of FIG. 1, FIG. 2, FIG. 3, and FIG. 4, as well as the flow diagrams in FIG. 9A, FIG. 9B, FIG. 9C, FIG. 10A, FIG. 10B, FIG. 10C and FIG. 11, a method for using the apparatus 100 to remove the cover 116 of the container 114. The method comprises using the sensor 160 to detect an orientation of the gripping area 301, and to communicate with the controller 140 over control line 150. The method further comprises planning the trajectory of the container 114 using the controller 140 so that gripping apparatus 113 can access the gripping area 301.

Figure 9A:
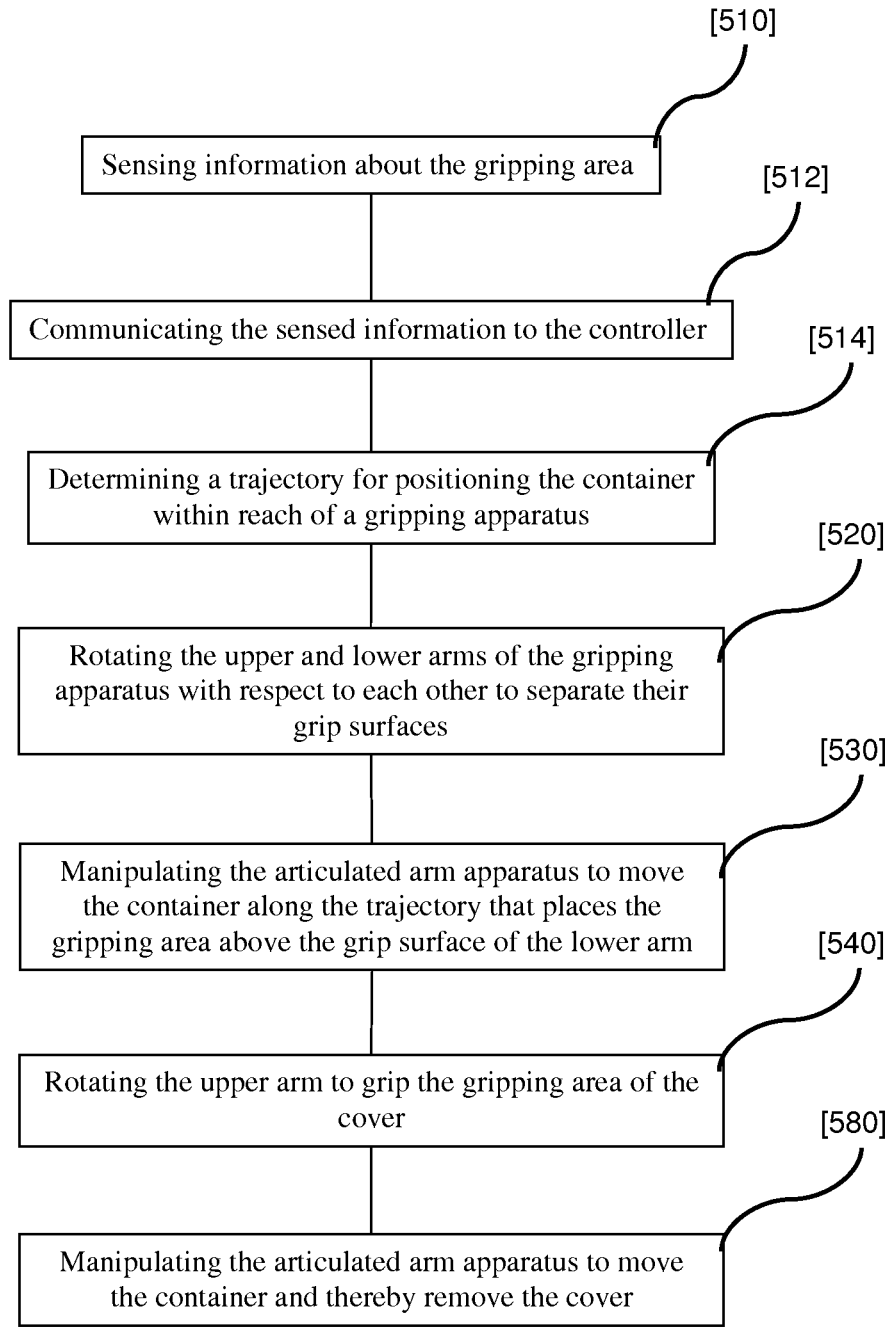
FIG. 9A is a flow diagram for a method to remove a cover of a container in a controlled environment enclosure.
Figure 9B:
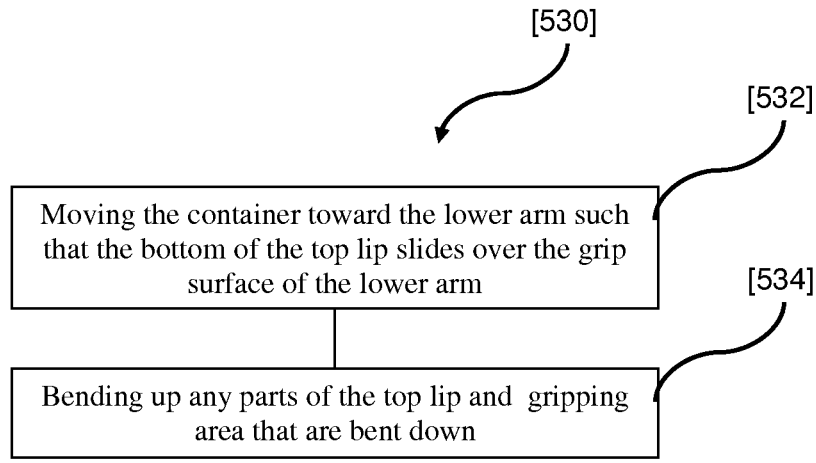
FIG. 9B is a more detailed flow diagram of part of the method of FIG. 9A.
Figure 9C:
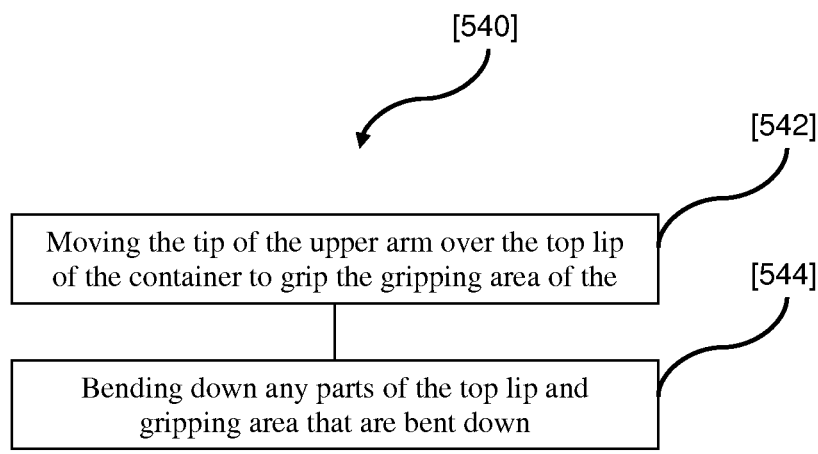
FIG. 9C is a more detailed flow diagram of part of the method of FIG. 9A.

In one example embodiment, shown in FIG. 9A and expanded on in FIG. 9B and FIG. 9C, the method comprises the sensor 160 sensing [510] information concerning the gripping area 301 and communicating [512] the sensed information to the controller 140 over control line 150. The sensed information can be the position of the gripping area 301 or the orientation of gripping area 301 or both. The sensed information can be used as input information by the controller 140 for determining [514] a trajectory for the articulated arm apparatus 115 along which to position the sealed container 114 within a reach of the gripping apparatus 113.

The cover gripping sequence can be initiated by rotating [520] the upper arm 406 and the lower arm 404 of the gripping apparatus 113 with respect to each other by an angle that separates the mutually facing grip surfaces 407 and 408 located on respectively lower arm 404 and upper arm 406 by at least the width of the container 114. This can be done by rotating one or both of the arms 406 and 404.

The method further comprises manipulating [530] articulated arm apparatus 115 to move the container 114 along the trajectory that places the gripping area 301 above the grip surface 407 of the lower arm 404. This has the result of moving [532] the container 114 towards the lower arm 404 in a trajectory that results in a bottom surface of the top lip 302 of container 114 nearing or contacting the grip surface 407 of the lower arm 404. At least during the last section of the approach, the container 114 can be moved to cause the bottom surface of the top lip 302 to substantially slide along the grip surface 407 of the lower arm 404. During this section of the approach, the tip of the lower arm 404 can be bending [534] the gripping area 301 upward in the case where gripping area 301 happens to be orientated downward to below the top lip 302.

The method further comprises rotating [540] upper arm 406 to grip the gripping area 301. This comprises moving [542] the tip of upper arm 406 comprising the surface 408 over the container cover 116 during its travel to the gripping area 301. As the upper arm 406 approaches the gripping area 301, it can slide over the container cover 116 above the top surface of top lip 302. During this action, the tip of the upper arm 406 can be bending [544] down to a substantially horizontal orientation any upward bent parts of cover 116, including specifically the gripping area 301.

Figure 10A:
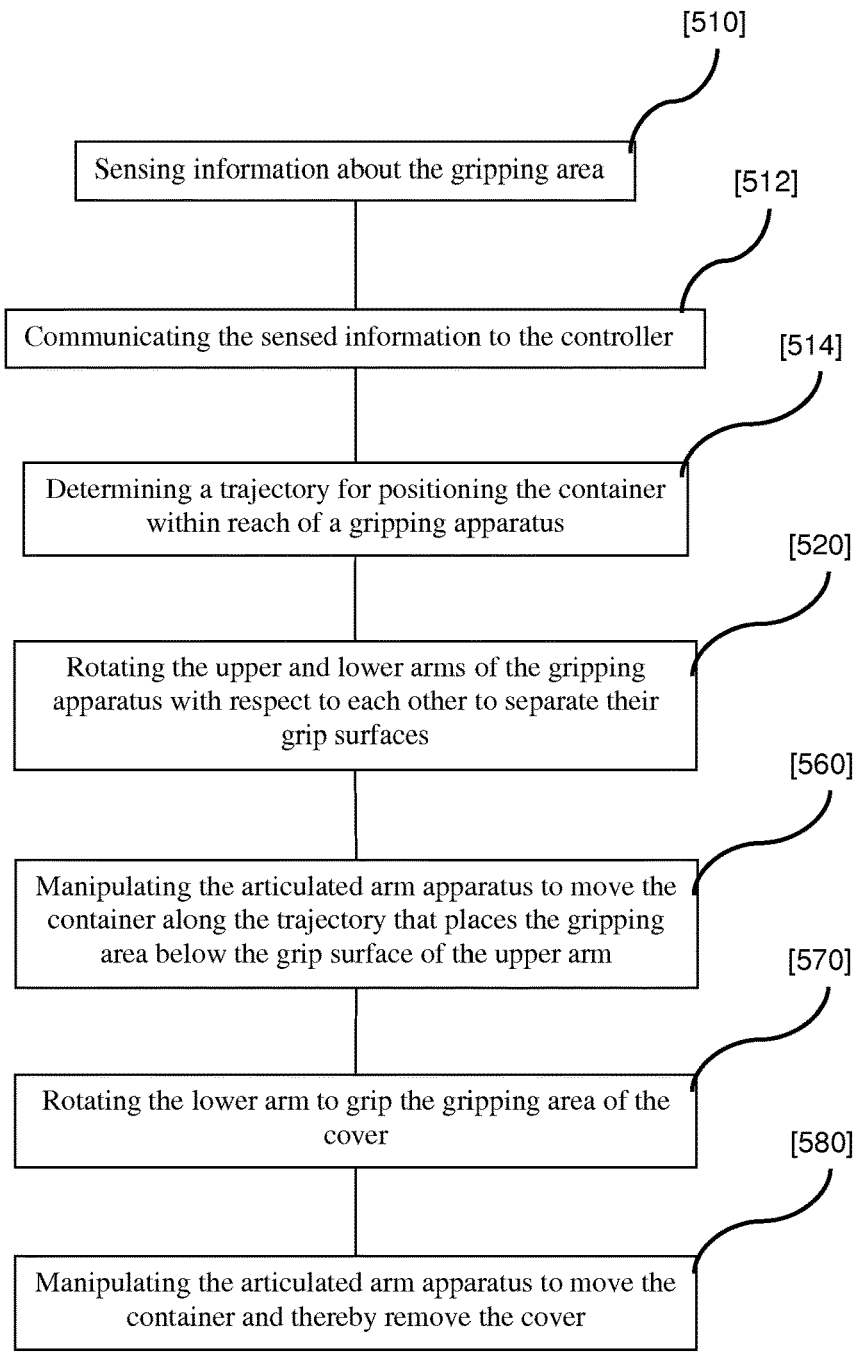
FIG. 10A is a flow diagram for a further method to remove a cover of a container in a controlled environment enclosure.
Figure 10B:
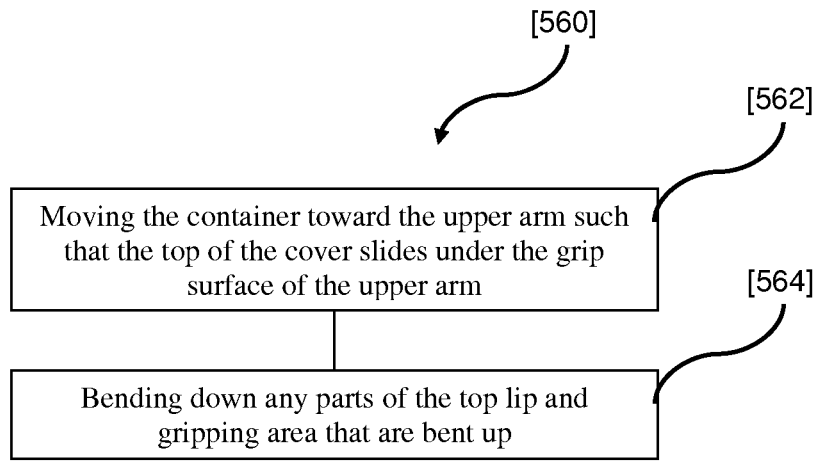
FIG. 10B is a more detailed flow diagram of part of the method of FIG. 10A.
Figure 10C:
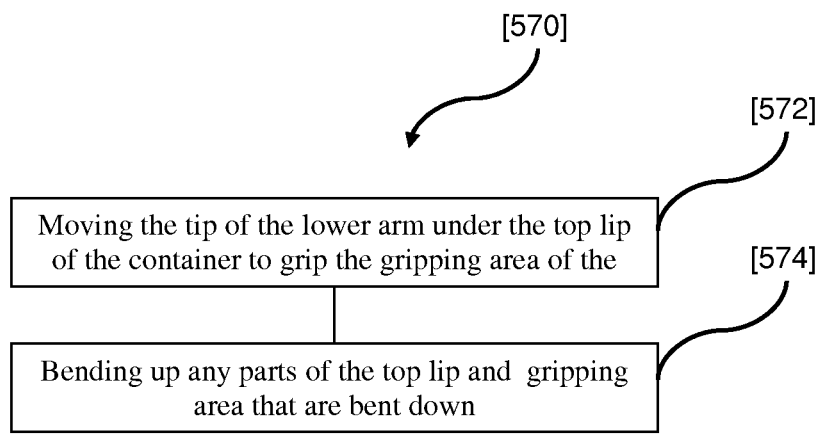
FIG. 10C is a more detailed flow diagram of part of the method of FIG. 10A.
Figure 11:
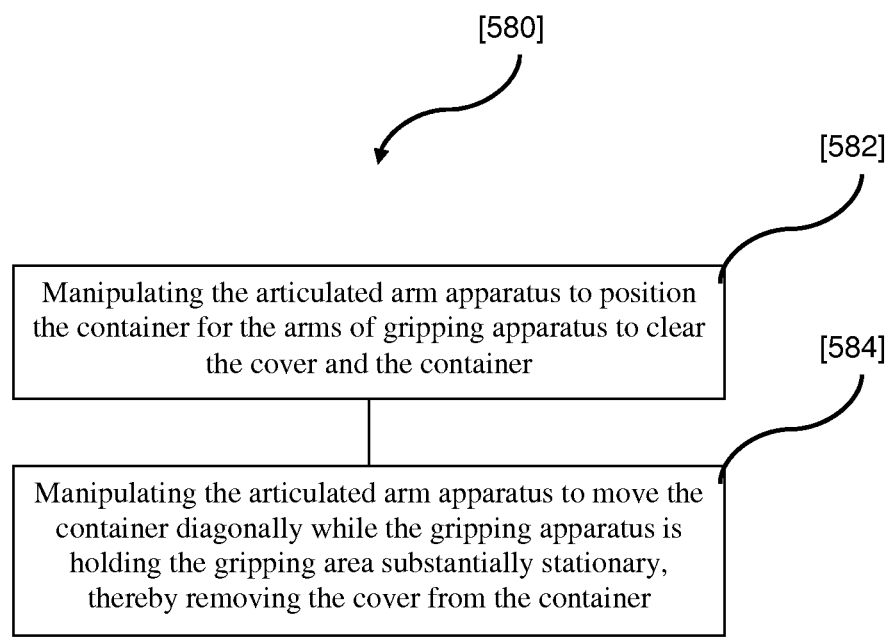
FIG. 11 is a more detailed flow diagram of part of FIG. 9A and FIG. 10A.

In another example embodiment of the method, shown in FIG. 10A and expanded on in FIG. 10B and FIG. 10C, the sensor 160 also senses the orientation of the gripping area 301 and communicates the sensed orientation to the controller 140 over control line 150. The sensed orientation of the gripping area 301 can, as before, be used as input information by controller 140 to determine a trajectory for the articulated arm apparatus 115 along which to position the sealed container 114 within a reach of the gripping apparatus 113.

The cover gripping sequence can, as above, be initiated with the rotating [550] of the upper arm 406 and the lower arm 404 of the gripping apparatus 113 with respect to each other by an angle that separates the mutually facing grip surfaces 407 and 408 located on respectively lower arm 404 and upper arm 406 by at least the width of the container 114.

The method further comprises manipulating [560] articulated arm apparatus 115 to move the container 114 along the trajectory that places the gripping area 301 below the grip surface 408 of the upper arm 406. This has the result of moving [562] the container 114 towards the upper arm 406 in a trajectory that results in a top surface of the top lip 302 of container 114, covered by cover 116, nearing or contacting the grip surface 408 of the upper arm 406. At least during the last section of the approach, the container 114 can be moved to cause the top surface of the top lip 302, covered by cover 116, to substantially slide along the surface 408 of the upper arm 406. During this section of the approach, the tip of the upper arm 406 can be bending [564] the gripping area 301 downward in the case where gripping area 301 happens to be orientated upward to above the top lip 302.

The method further comprises rotating [570] the lower arm 404 to grip the gripping area 301. This comprises moving [572] the tip of lower arm 404 comprising the grip surface 407 under the bottom surface of top lip 302 during its travel to the gripping area 301. As the lower arm 404 approaches the gripping area 301, it can slide along the bottom surface of top lip 302. During this action, the tip of the lower arm 404 can be bending [574] up to a substantially horizontal orientation any downward bent parts of cover 116, including specifically the gripping area 301.

The gripping apparatus 113 works for a wide range of thickness of the container cover 116 by clamping the gripping area 301 of container cover 116 in between the mutually facing grip surfaces 407 and 408 located on respectively the lower arm 404 and the upper arm 406.

The method provides for removing [580] the container cover 116 in the controlled environment enclosure 420. This is shown in expanded form in FIG. 11. Once the gripping apparatus 113 has gripped the gripping area 301 and is holding the gripping area 301 substantially stationary, the method can proceed further with manipulating [582] the articulated arm apparatus 120 to either lower the container 114 or rotate the container 114 about an axis substantially in the plane of the cover. This manipulating [582] is to a degree that positions and/or orients the container 114 and cover 116 such that clearance is established for the two arms 404 and 406 of the gripping apparatus 113 to clear the cover 116 and container 114 during the subsequent removal of the cover 116 from the container 114.

Referring to the articulated arm apparatus 115 and the gripping apparatus 113 as shown in FIGS. 5-8, the container cover 116 can be removed by moving the container 114 in a substantially diagonal trajectory by manipulating [584] articulated arm apparatus 115 while the gripping apparatus 113 is holding the gripping area 301 substantially stationary. The term "substantially diagonal is used in this specification to describe a direction of motion parallel to the diagonal of the container 114 between the two sides of the container 114 that terminate jointly at the location of the gripping area 301. The substantially diagonal trajectory minimizes a total length of adhesive that is being opened at any given time. As shown in FIGS. 5-8, the substantially diagonal trajectory can be obtained by rotating the articulated arm apparatus 115 in direction A. This particular choice of motion can keep all moving parts participating in removing the container cover 116 confined to a small space within the controlled environment enclosure 420. The controller 140 can be configured for predetermining the small space before the motion is conducted by predetermining the path for the container 114 to follow while being held by the articulated arm apparatus 115. The predetermined path can be, but is not limited to, a circular path.

In another embodiment the container cover 116 can be removed by a more general direction of motion of container 114 by manipulating [584] articulated arm apparatus 115 while the gripping apparatus 113 is holding the gripping area 301 substantially stationary. In this embodiment the articulated arm apparatus 115 is not limited to being rotated. This motion of the container 114 can be executed in a fashion and direction such as to remove the container cover 116 simultaneously along two edges of the container 114, starting from the gripping area 301.

FIGS. 5-8 provide an example of removal of the container cover 116 by a pushing motion of articulated arm apparatus 115. In a further embodiment, the container cover 116 can be removed in a pulling motion by articulated arm apparatus 115.

The sensor 160 can be used for verifying the completeness of removal of the container cover 116. If, for some undetermined reason, the gripping apparatus 113 were to lose its grip on the container cover 116 during the removal of the container cover 116, the articulated arm apparatus 115 can continue moving the container 114 with the partially removed container cover 116. In the event of such partial removal of container cover 116; the previously described process of orienting substantially horizontally any up- or downward bent areas of the cover 116, including the gripping area 301, can be repeated after the articulated arm apparatus 115 repositions the gripping area 301 near the tip of the lower arm 404. If the gripping area 301 were to be no longer available, for example if the gripping area 301 were torn off, the process of gripping the gripping area 301 can be repeated after redirecting the articulated arm apparatus 115 to another suitable available gripping area 301.

For the sake of clearly differentiating between the different manipulations that are undertaken by the articulated arm apparatus 120, we refer to the manipulating [584] of the articulated arm apparatus 120 to remove the cover 116 as a "first manipulation", and the manipulating [530] and [560] of the articulated arm apparatus 120 to position the container 114 between the lower arm 402 and the upper arm 406 as a "second manipulating", while we refer to the manipulating [582] of the articulated arm apparatus 120 to lower the container 114 or to rotate the container 114 about an axis substantially in the plane of the cover 116 as a "third manipulating". The gripping apparatus 113 is not limited to the example shown in FIG. 4. In other embodiments the gripping apparatus 113 can comprise a pair of prongs with narrow gap in between, one of which slides over and the other slides under the gripping area, thereby clamping the cover by friction caused by rotation of both prongs. In yet another embodiment the gripper can be of the type described in German Patent DE4419475, hereby incorporated herein by reference. In yet other embodiments the gripper apparatus can comprise gripping devices that are commercially available, such as parallel grippers, angular grippers or inflatable bellow grippers.

Additional Notes

The drawings and the associated descriptions are provided to illustrate embodiments of the invention and not to limit the scope of the invention. Reference in the specification to "one embodiment" or "an embodiment" is intended to indicate that a particular feature, structure, or characteristic described in connection with the embodiment is included in at least an embodiment of the invention. The appearances of the phrase "in one embodiment" or "an embodiment" in various places in the specification are not necessarily all referring to the same embodiment.

As used in this disclosure, except where the context requires otherwise, the term "comprise" and variations of the term, such as "comprising," "comprises" and "comprised" are not intended to exclude other additives, components, integers or steps.

In the foregoing specification, the invention has been described with reference to specific embodiments thereof. It will, however, be evident that various modifications and changes may be made thereto without departing from the broader spirit and scope of the invention. The specification and drawing are, accordingly, to be regarded in an illustrative rather than a restrictive sense. It should be appreciated that the present invention should not be construed as limited by such embodiments.

From the foregoing description it will be apparent that the present invention has a number of advantages, some of which have been described herein, and others of which are inherent in the embodiments of the invention described or claimed herein. Also, it will be understood that modifications can be made to the device, apparatus and method described herein without departing from the teachings of subject matter described herein. As such, the invention is not to be limited to the described embodiments except as required by the appended claims.

PARTS LIST 100 apparatus
113 gripping apparatus
114 container
115 articulated arm apparatus
116 container cover
120 controlled environment enclosure
140 controller
150 control line
160 sensor
121 window
130 inlet filter
131 inlet valve
132 blower
133 outlet filter
134 outlet valve
201 step
301 gripping area
302 top lip
401 base flange
402 radial seal
403 main shaft
404 lower arm
405 radial seal
406 upper arm
407 grip surface
408 grip surface
[510] sensing the orientation of the gripping area
[512] communicating the sensed orientation to
[514] determining a trajectory
[520] rotating the upper arm and the lower arm with respect to each other
[530] manipulating the articulated arm apparatus
[532] moving the container toward the lower arm
[534] bending up the gripping area
[540] rotating the upper arm to grip the gripping area
[542] moving the tip of the upper arm over the container cover
[544] bending down bent parts of the cover including the gripping area
[550] rotating the upper arm
[560] manipulating the articulated arm apparatus
[562] moving the container toward the upper arm
[564] bending down the gripping area
[570] rotating the lower arm to grip the gripping area
[572] moving the tip of lower arm under the bottom surface of the container top lip
[574] bending up bent parts of the cover including the gripping area
[580] removing the container cover
[582] manipulating the articulated arm apparatus to establish clearance for arms
[584] moving the container in a substantially diagonal trajectory

What is claimed is:

1. A method for removing within a controlled aseptic environment enclosure a container cover from a sealed container, the sealed container sealed by the container cover, the method comprising moving the container while holding a gripping area of the container cover stationary wherein moving the container comprises holding the container with an articulated arm apparatus disposed within the controlled aseptic environment; and removing the container cover is achieved by moving the container with respect to the gripping area during a first manipulation of the articulated arm apparatus.

2. The method of claim 1, further comprising positioning along a trajectory the sealed container within a reach of a gripping apparatus disposed within the controlled environment by a second manipulation of the articulated arm apparatus; and gripping the gripping area with the gripping apparatus.

3. The method of claim 2, wherein the positioning the sealed container comprises placing the gripping area of the container cover between two gripping elements of the gripping apparatus, the first and second of the two gripping elements respectively comprising first and second mutually parallel and mutually engagable grip surfaces.

4. The method of claim 3, further comprising rotating at least one of the gripping elements.

5. The method of claim 4, wherein the positioning the gripping area between the two gripping elements comprises placing the gripping area proximate and facing the first grip surface.

6. The method of claim 5, wherein the rotating at least one of the gripping elements comprises moving the second of the two gripping elements in a plane parallel to the first grip surface.

7. The method of claim 6, wherein the positioning further comprises straightening the gripping area if the gripping area is bent toward the first grip surface by contacting to the first grip surface to one of the gripping area and a part of the cover in contact with the gripping area.

8. The method of claim 7, wherein the moving the second gripping element comprises straightening the gripping area if the gripping area is bent toward the second gripping element by contacting the second grip surface to the other of the gripping area and the part of the cover in contact with the gripping area.

9. The method of claim 2, further comprising at least one of lowering the container and rotating the container about an axis in a plane, defined by the cover by a third manipulation of the articulated arm apparatus.

10. The method of claim 9, wherein the at least one of rotating and raising the gripping area is to an extent that allows the gripping apparatus to remain clear of the container during the removing the container cover.

11. The method of claim 2, wherein the removing the container cover is removing the container cover simultaneously along two edges of the container.

12. The method of claim 2, wherein the first manipulation of the articulated arm apparatus comprises moving the container with respect to the gripping apparatus.

13. The method of claim 12, where in the moving the container with respect to the gripping apparatus comprises moving the container along a predetermined path within a predetermined space.

14. The method of claim 13, wherein at least one of the predetermined path and the predetermined space is determined using a controller.

15. The method of claim 13, wherein the predetermined path is a circular path.

16. The method of claim 2, wherein the moving the container with respect to the gripping apparatus comprises moving the container diagonally with respect to the gripping apparatus.

17. The method of claim 2, wherein the trajectory is based on information obtained from a sensor.

18. The method of claim 17, wherein the information comprises at least one of position information and orientation information about the gripping area.

19. The method of claim 2, further comprising inspecting the container cover using a sensor.

20. The method of claim 19, further comprising
    selecting an alternative gripping area of the container cover based on the inspecting;
    gripping the alternative gripping area with the gripping apparatus; and
    removing the container cover by moving the container.

21. The method of claim 2, further comprising moving the gripping apparatus away from an operational area of the articulated arm apparatus after removing the container cover.

* * * * *